United States Patent [19]

Chen

[11] Patent Number: 4,706,015

[45] Date of Patent: Nov. 10, 1987

[54] METHOD AND CIRCUIT FOR REDUCING CONTACT RESISTANCE OF THE POTENTIAL PROBES OF A FOUR-POINT-PROBE IN CONTACT WITH A III-V COMPOUND SEMICONDUCTOR WAFER

[76] Inventor: James T. C. Chen, 1526 Cherrywood Dr., San Mateo, Calif. 94403

[21] Appl. No.: 817,460

[22] Filed: Jan. 9, 1986

[51] Int. Cl.$^4$ .............................. G01R 27/14
[52] U.S. Cl. .................. 324/64; 324/158 D
[58] Field of Search ............ 324/64, 62, 158 D, 158 T

[56] References Cited

U.S. PATENT DOCUMENTS 3,048,776 8/1962 Logan ................................ 324/64
3,443,222 5/1969 Mildwater ........................... 324/64

OTHER PUBLICATIONS

Barry et al, Circuit to Facilitate the Measurement by the Four-Probe Method of the Resistivity of Silicon in the Range 0.002 to 10,000 ohm-cm, J. Sci. Instrum., 1962, vol. 39, pp. 119-121.

Allen et al, An AC Silicon Resistivity Meter, the Review of Scientific Instruments, 4-1961.

Primary Examiner—Reinhard J. Eisenzopf
Assistant Examiner—Jack B. Harvey
Attorney, Agent, or Firm—Allston L. Jones

[57] ABSTRACT

A method and circuit to enable Four-Point Probe and Spreading Resistance techniques to overcome the high contact resistance in measuring the resistivities of III-V compound semiconductors. This is accomplished by using forward DC bias to greatly reduce the contact resistance of the potential probe to the III-V semiconductor while maintaining the AC input impedance of the potential probe to be several orders of magnitude higher than the DC input resistance, thus enabling use of the AC component to make potential measurements very accurately.

14 Claims, 1 Drawing Figure

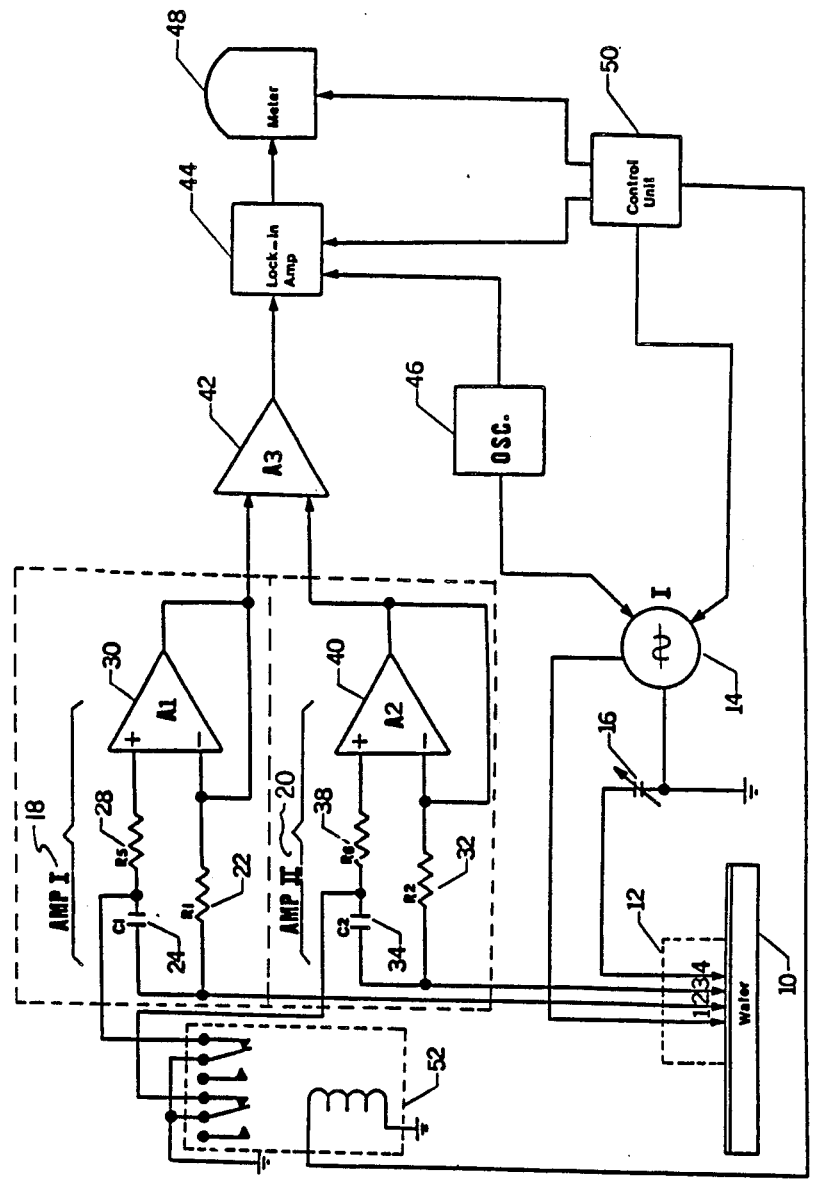

METHOD AND CIRCUIT FOR REDUCING CONTACT RESISTANCE OF THE POTENTIAL PROBES OF A FOUR-POINT-PROBE IN CONTACT WITH A III-V COMPOUND SEMICONDUCTOR WAFER

BACKGROUND OF THE INVENTION

This invention relates to resistivity measurement devices, and more particularly, devices for measuring the resistivity of a surface layer of semiconductor wafers including III-V compound semiconductors.

Most Four-Point-Probe resistivity meters currently available can measure absolute sheet resistivities of Si, Ge or metal films up to $10^6$ ohm/sq with good accuracy except for the lightly implanted layers on an opposite type substrate. However, no known commercially available Four-Point-Probe units works on the III-V compound semiconductors at dosages below $10^{18}$ cm$^3$. This is generally due to the resistance of the contact between the metal point probe and the nondegenerated III-V compound semiconductor being so high that the voltmeter connected between any of the two potential probes of the Four-Point-Probe can not pick up the potential at the probed spot on the semiconductor with less than 0.01% error. This accuracy is required in order to see the small difference of the potentials at the probed spots on the III-V compound semiconductor surface.

For a Four-Point-Probe to make a measurement with less than 1% error, the contact resistance of any of its potential probe to the semiconductor contacts should be less than about $10^{-5}$ times of input resistance of the potential probe. This is due to the potential difference between the two potential probes being as small as $10^{-3}$ times their potential from ground. Therefore, if the input resistance of the potential probe is $10^{14}\Omega$, the contact resistance of the potential probe must be below $10^9\Omega$.

The contact resistivity of tungsten to a 2$\Omega$-cm, N type Si is about $5\times10^4\Omega$/cm$^2$ at zero bias. This means $5\times10^9\Omega$ for a area of $1000\mu^2$ which is a typical metal probe to semiconductor contact area. When the Silicon resistivity is increased 100 times, its contact resistance to a metal is increased roughly one order of magnitude. Therefore, for intrinsic Si which may have a resistivity of about $2\times10^4\Omega$-cm, the corresponding contact resistance can be about $5\times10^{11}\Omega$.

Probe pressure and field concentration in the semiconductor near the probe tip may reduce the contact resistance up to two orders of magnitude but some foreign material may be present at the contact interface to increase the contact resistance. In any case, a Four-Point-Probe Meter with the input resistance of $10^{14}\Omega$ at the potential probes can barely be used to measure the resistivity of intrinsic single-crystal Si. The contact resistivity of a metal to a III-V compound semiconductor, such as GaAs, is more than 2 orders of magnitude higher than that to Si, therefore even the more advanced Four-Point-Probe mentioned above has problems in making a clean measurement of GaAs, with the resistivity about a few $\Omega$-cm. One may, however, reduce the contact resistance by 7 orders of magnitude by applying a 0.5 v forward bias to the contact. Unfortunately, in doing so, the input resistance of the potential probe has to be reduced to one or two orders of magnitude higher than the contact resistance, at its highest, so that the contact can take a large enough bias across it. This is far less than what is desirable, namely 5 orders of magnitude higher than the contact resistance.

It is well known that the technologies and applications of microwave devices, high speed ICs and photovoltaic devices using III-V compound semiconductors as the materials are still in the stages of rapid growth. Obviously, a wider range, faster, more repeatable and more accurate way of measuring the resistivities or sheet resistivities of III-V compound semiconductors for process controls, and for material evaluation would prove helpful to these technologies. The method and circuit of the present invention overcome the high contact resistance problem of probing III-V compound semiconductor wafers and provides an accurate resistivity measurement using a four-point probe or spreading resistance probe.

SUMMARY OF THE INVENTION

In accordance with the illustrated embodiment, the present invention provides a method and circuit for accurately measuring the resistivity of III-V compound semiconductor wafers. The method of the present invention includes a composite DC and low frequency AC current applied to the current supplying probes of a four-point-probe in contact with the wafer.

In the composite current, the magnitude of the DC component is greater than one half of the peak-to-peak magnitude of the AC component. Means are coupled to each of the potential monitoring probes of the four-point-probe to accurately isolate the AC component and to provide DC bias at each probe. The isolated AC potential components are then compared to form a difference signal that is proportional to the resistivity of the wafer.

The isolation of the AC component of the composite potential at the probes includes a blocking capacitor serially connected to the non-inverting input terminal of an opamp voltage follower of extremely low input bias current, high input impedance, high gain and high common mode rejection ratio. When the measurement is in progress, the input of the voltage follower is connected only to the blocking capacitor so that the input impedance is not reduced by having any component in parallel with it. The DC level at the input of the voltage follower is kept constant during measurement because the bias current is too low to make any noticeable change of the charge in the blocking capacitor. When the measurement is not in progress, the input of the voltage follower is connected to a constant DC source which may be at zero volts. The DC component at the output of the voltage follower is therefore kept at the level of the DC source at all times, while the AC component at the output follows the AC potential at the probes accurately. A DC bias bleeding resistor of the order of one meg ohms is connected from the probe to the output of the voltage follower. This resistor is low enough to provide sufficient DC bias current to the probes for lowering their contact resistance with the wafer, yet it is guarded against bleeding the AC current through it. Thus the AC input impedance of the probes remain several orders of magnitude higher than the bleeding resistor and is high enough to be used with a potential probe of a four-point probe or spreading resistance measurement.

DESCRIPTION OF THE FIGURE

The FIGURE shows a schematic/block diagram of the circuit of the present invention.

DESCRIPTION OF THE PREFERRED EMBODIMENT

Referring to the FIGURE there is shown a four-point probe and resistivity meter configuration of the present invention that is capable of accurately measuring the sheet resistivity of semiconductor wafers typically present with III-V compound semiconductors. The circuit configuration shown includes a four-point probe 12, of a typical configuration, interfacing with the surface of a semiconductor wafer 10. A composite AC-DC current source 14 is connected between probe 1 and ground, and a variable DC voltage source 16 is connected between ground and probe 4 to bias wafer 10 at a selectable potential above ground. Potential measuring probes 2 and 3 are each shown connected to the input terminal of identical DC rejection/unity gain AC amplifiers 18 and 20, respectively. The output terminals of amplifiers 18 and 20, in turn, are connected to the input terminals of difference amplifier 42 which has its output terminal connected to a first input terminal of lock-in amplifier 44 (e.g. phase lock amplifier). Coupled to a second input terminal of lock-in amplifier 44 is an output signal from oscillator 46 wherein the frequency of this signal is the same as the frequency of the signal that oscillator 46 applies to current source 14. Restated, the frequency of the AC component of the current applied to wafer 10 via probe 1 is the same as the frequency of the signal applied to lock-in amplifier 44 to selectively eliminate any noise component of the output signal from difference amplifier 42. The output signal from lock-in amplifier 44 is then applied to DC voltmeter 48 for measurement and display. Since the sheet resistivity of wafer 10 is proportional to the output voltage potential of lock-in amplifier 44, a scale could be provided on meter 48 to provide a direct read-out as to the measured resistivity. In addition, an optional control unit 50 and relay 52 are shown with the control unit having output signals applied to the current generator 14, the lock-in amplifier 44, the meter 48, and the coil of relay 52.

The first DC rejection/unity gain AC amplifier 18 includes a high input impedance, high gain operational amplifier (A1) 30, a shunt input resistor (R1) 22 connected between probe 2 and the output terminal of op amp 30, a capacitor (C1) 24 having one end connected to probe 2, and a series resistor (R5) 28 connected between the other end of capacitor 24 and the non-inverting input terminal of op amp 30. In addition, op amp 30 is connected in the unity gain configuration, with its inverting input terminal connected to its output terminal. The second DC rejection/unity gain AC amplifier 20 is similarly configured to that of amplifier 18 with resistor (R2) 32, capacitor (C2) 34, resistor (R6) 38, and op amp 40 corresponding, respectively, to resistor (R1) 22, capacitor (C1) 24, resistor (R5) 28, and op amp 30.

In operation, DC voltage source 16 is adjusted to forward bias wafer 10 with respect to probes 2 and 3 sufficiently so that the DC current flow therethrough substantially reduces the contact resistance between probes 2 and 3 and wafer 10. The composite current source 14 is also adjusted to produce a current having a DC component value that is greater than one half of the peak-to-peak value of the AC component of that produced current. The AC component of this current is controlled by oscillator 46. By experimentation it was found that accurate measurements are obtained with a frequency of about 10 Hz, however, any frequency up to several hundred to one thousand Hertz would produce similar results. The composite current is applied to probe 1; the AC component flows through wafer 10 to probe 4, and then to ground via DC voltage source 16, while the DC component also flows to probes 2 and 3.

Probes 2 and 3 are provided to measure the AC potential at two points on wafer 10. Probes 2 and 3 are each provided with an AC and a DC path through the input networks of amplifiers 18 and 20, respectively. At this point your attention is directed to probe 2 and amplifier 18 for a detailed discussion of its operation. It is to be understood that probe 3 and amplifier 20 function in the same way by virtue of the similarities of the construction of amplifiers 18 and 20.

The DC signal path associated with probe 2 is through resistor (R1) 22 to the output terminal of op amp (A1) 30 which is adjusted to be at, or near, DC ground potential. Therefore, a DC voltage provided by DC voltage source 16 should be shared by the contact at probe 2 and resistor (R1) 22 which can have a value of about $10^6 \Omega$. This voltage (Vw) will force the contact resistance at probe 2 to be comparable or lower than $10^6 \Omega$, since whenever the resistance tends to be higher than $10^6 \Omega$, more of Vw will be forward biased across the contact and force a drastic reduction in contact resistance. In addition, since the AC potential at both ends of resistor (R1) 22 is Vw, no Ac current flows throiugh resistor R1, thus resistor R1 is said to be guarded.

Although op amp (A1) 30 is in a unity gain configuration, the DC input impedance of probe 2 equals the value of resistor (R1) 22, the AC input impedance of probe 2 is about $10^6$ times higher than the value of resistor (R1) 22, provided that the input impedance of op amp (A1) 30 is higher than the value of $R1 \times 10^6$ and that the open loop gain of op amp (A2) 40 is higher than $10^6$. This is due mainly to the feedback from the output terminal of op amp (A1) 30 to resistor (R1) 22, results in a $10^{12} \Omega$ AC input impedance. That allows for Four-Point-Probe measurements with better than 1% accuracy if the contact resistance is less than $10^7 \Omega$. Therefore, this design solves the problem of high contact resistance of Four-Point-Probes to III-V compound semiconductors.

The output signals from op amps 30 and 40 are coupled to alternate input terminals of difference amplifier 42 where a AC signal proportional to the difference between the AC components of the potential on probes 2 and 3 is generated. The difference signal from amplifier 42 and a signal from the same source as the AC current component from generator 14 are applied to lock-in amplifier 44 to exclude any noise in the difference signal. The final step is to apply the noise reduced difference signal generated by lock-in amplifier 44 to a meter 48 (e.g. a DC voltmeter) for display of the potential difference or directly in ohms/square.

Also shown in the FIGURE is an optional control unit 50 and relay 52. The control unit 50 could be used to provide automatic range adjustment for various resistivity measurements or various materials. It can also control the application of the AC signal from current source 14 and ground the input terminals of op amps 30 and 40, via relay 52, when the AC signal component is not present. To reapply the AC signal, the AC source is gradually turned-on to the desired level.

The present invention not only simultaneously forces low contact resistances and provides high input impedance at the potential probes 2 and 3, but also is capable of detecting weak signals by means of the lock-in amplifier 44. Therefore, the present invention makes it possible to measure semiconductor samples having low resistivity values without the necessity of large currents. By avoiding large currents, probe tip damage, heating, and biasing effects on the wafer are avoided.

From the foregoing description, it will be apparent that the invention disclosed herein provides a novel and advantageous four-point-probe resistivity measuring device for measuring semiconductors with high contact resistance and method for measuring semiconductor wafers having low sheet resistivity. As will be understood by those familiar with the art, the invention may be embodied in other specific forms without departing from the spirit or essential characteristics thereof.

What is claimed is:

1. A method for measuring the resistivity of a wafer of a III-V compound semiconductor using a four-point-probe disposed to contact the surface of the wafer, said method comprising the steps of:
   a. applying a composite DC and low frequency AC signal between a first probe and a fourth probe of the four-point probe wherein the magnitude of the DC signal component is at least one half of the peak-to-peak magnitude of the AC signal component plus a selected DC level to apply a DC bias to the wafer;
   b. rejecting the DC potential component and isolating the AC potential component of the composite DC/AC wafer signal at each of a second and third probe of said four-point probe to reduce the resistance between each of said second and third probes and their respective contact point with the wafer; and
   c. comparing the AC potential components isolated in step b. to form an AC difference signal therefrom that is proportional to the resistivity of the wafer.

2. A method as in claim 1 further including the step of:
   d. applying the difference signal of step c. and an AC signal of the same frequency as the AC current component of step a. to a lock-in amplifier to minimize the noise components of the difference signal of step c. to create a reduced noise difference signal.

3. A method as in claim 1 further including the step of:
   e. displaying the measured resistivity of the wafer.

4. A method as in claim 2 further including the step of:
   f. displaying the measured resistivity of the wafer.

5. A method as in claim 1 wherein the DC signal component of step a. is applied such that the second and third probes of said four-point-probe are forward biased with respect to the wafer.

6. A method as in claim 1 wherein step b. includes the steps of:
   g. terminating individually the DC potentials on the second and third probes into a blocking capacitor and a high impedance shunt resistive load;
   h. passing individually the AC potentials on the second and third probes through the DC blocking capacitor; and
   i. amplifying individually the AC potential passing through the blocking capacitors of step h. with a high input impedance, high gain amplifier whose output voltage guards the high impedance shunt resistive load of step g.

7. A method as in claim 6 wherein step b. further includes the step of connecting the DC blocking capacitor
   to ground when measurements are not being made to maintain a substantially DC ground potential as the output signal of the amplifier of step i.

8. A circuit for measuring the resistivity of a wafer of a III-V compound semiconductor, the circuit comprising:
   four-point probe means having first, second, third and fourth probes spaced apart from each other, each of said four probes being disposed to make physical and electrical contact with said wafer;
   source means for applying a composite DC and low frequency AC signal between the first and fourth probes wherein the magnitude of the DC signal component is at least one half of the peak-to-peak magnitude of the AC signal component plus a selected DC level to apply a DC bias to the wafer when contact is made;
   high input impedance means for rejecting the DC potential component and isolating the AC potential component of the composite DC/AC signal applied to the wafer at each of the second and third probes to reduce the resistance between each of said second and third probes and their respective contact point on the wafer; and
   comparing means for comparing the AC potential components isolated by the high input impedance means to form an AC difference signal therefrom that is proportional to the resistivity of the wafer.

9. A circuit as in claim 8 wherein:
   said source means includes:
   an oscillator for generating a signal of the selected low frequency for the AC component of the composite signal; and
   DC signal generator means; and
   said circuit further includes a lock-in amplifier responsive to the difference signal from the comparing means and the low frequency signal from the oscillator to form a reduced noise difference signal.

10. A circuit as in claim 8 further includes means responsive to the difference signal for displaying the measured resistivity of the wafer.

11. A circuit as in claim 9 further includes means responsive to the reduced noise difference signal for displaying the measured resistivity of the wafer.

12. A circuit as in claim 8 wherein the high input impedance means includes:
    a pair of differential input amplifiers each having unity gain and a high input impedance;
    a pair of blocking capacitors, one each, coupled serially between the non-inverting input terminal of one of said amplifiers and a different one of said second and third probes; and
    a pair of high impedance resistors, one each, having one end connected to the inverting input and output terminals of one of said amplifiers and the other end connected to a different one of said second and third probes;
    each of said amplifiers having an input impedance that is several orders of magnitude greater than the impedance of each of said high input impedance resistors to maintain the DC bias of the wafer to minimize contact resistance between the second and third probes and the wafer, and to minimize AC current flow through the second and third probes.

13. A circuit as in claim 12 wherein:
the high input impedance means further includes second and third probes; and
two DC rejection/AC follower amplifiers each of which include:
- a high input impedance, high gain operational amplifier;
- a first high impedance resistor coupled between the corresponding one of said second and third probes and the output terminal of the operational amplifier;
- a capacitor having one end connected to the corresponding one of said second and third probes; and
- a second pair of resistors, one each, coupled between the non-inverting input terminal of one of the amplifiers and the corresponding capacitor.

14. A circuit as in claim 13 wherein the high input impedance means further includes switch means for connecting the second and third probes to ground when measurements are not being made.

* * * * *